United States Patent [19]

Kim et al.

[11] Patent Number: 5,576,018
[45] Date of Patent: Nov. 19, 1996

[54] METHOD FOR TREATING NEUROLOGICAL DISORDERS

[75] Inventors: Sinil Kim, Solana Beach; Stephen B. Howell, Del Mar, both of Calif.

[73] Assignee: DepoTech Corporation, San Diego, Calif.

[21] Appl. No.: 484,501

[22] Filed: Jun. 7, 1995

Related U.S. Application Data

[62] Division of Ser. No. 62,799, May 14, 1993, Pat. No. 5,455,044.

[51] Int. Cl.$^6$ .................................................. A61K 9/127
[52] U.S. Cl. ........................................................... 424/450
[58] Field of Search ............................................. 424/450

[56] References Cited

U.S. PATENT DOCUMENTS

| | | |
|---|---|---|
| 4,078,052 | 3/1978 | Papahadjopoulos . |
| 4,089,801 | 5/1978 | Schneider . |
| 4,145,410 | 5/1979 | Sears . |
| 4,224,179 | 9/1980 | Schneider . |
| 4,235,871 | 11/1980 | Papahadjopoulos et al. . |
| 4,310,506 | 1/1982 | Baldeschwieler et al. . |
| 4,394,372 | 7/1983 | Taylor . |
| 4,522,803 | 6/1985 | Lenk et al. . |
| 4,588,578 | 5/1986 | Fountain et al. . |
| 4,599,227 | 7/1986 | Dees et al. . |
| 4,610,868 | 9/1986 | Fountain et al. . |
| 4,619,913 | 11/1986 | Luck et al. . |
| 4,752,425 | 7/1988 | Martin et al. . |
| 4,769,250 | 9/1988 | Forssen . |
| 4,781,871 | 11/1988 | West, III et al. . |
| 4,813,399 | 3/1989 | Gordon . |
| 4,920,016 | 4/1990 | Allen et al. . |
| 5,000,959 | 3/1991 | Iga et al. . |
| 5,021,200 | 6/1991 | Vanlerberghe et al. . |
| 5,077,056 | 12/1991 | Bally et al. . |
| 5,204,112 | 4/1993 | Hope et al. . |
| 5,211,955 | 5/1993 | Legros et al. . |
| 5,225,212 | 7/1993 | Martin et al. ............................ 424/450 |

FOREIGN PATENT DOCUMENTS

| | | |
|---|---|---|
| 2050287 | 1/1991 | United Kingdom . |

OTHER PUBLICATIONS

Huang, Biochemistry, 8:334–352, 1969, "Studies on Phosphatidylcholine vesicles formation and Physical characteristics."
Bang, M. Mol. Bio., 13–238–252, 1965, "Diffusion of univalent ions across the lamellae of swollen phospholipids."
Szoka, et al., Ann. Rev. Biophys, Bioeng., 9:465–508, 1980, "Comparative properties and methods of preparation of lipid vesicles (liposomes)."
Shakiba, et al., Investigative ophthalmology and visual Science, 34(10):2903 10, 1993 Sep., "Evaluation of retinal toxicity and liposome encapsulation of Anti–CMV Drug 2'–nor–cyclic GMP."
Frucht–Perry, et al., Cornea, 11(5):393–7, 1992 Sep., "Fibrin–enmeshed tobramycin liposomes: single application topical therapy of pseudomonas . . . ".
Assil, et al., Investigative Ophthalmology and Visual Science, 32(13):3216–20 1991 Dec., "Tobramycin liposomes. Single subconjunctival therapy of . . . ".
Assil, et al., Investigative Ophthalmology and Visual Science, 32(11):2891–7, 1991 Oct., Liposome suppression of proliferative vitreoretinopathy. Rabbit..
Turski, et al., Magnetic Resonance in Medicine, 7(2):184–96, 1988 Jun., "Magnetic resonance imaging of rabbit brain after intracarotid injection . . . ".
Skuta, et al., American Journal of Ophthalmology, 103(5): 714–16, 1987, May 15 "Filtering surgery in owl monkeys treated with the antimetabolite . . . ".
Assil, et al., Archives of Ophthalmology, 105(3):400–3, 1987 Mar., "Multivesicular liposomes. Sustained release of the antimetabolite . . . ".
Barbet, et al., Biochimica et Biophysica Acta, 772(3):347–356, 1984, May 30, "Weat acid–induced release of liposome–encapsulated carboxyfluorescein".
Kim, et al., Biochim. Biophys. Acta, 646:1, 1981, "Preparation of cell–size unilamellar liposomes with high captured volume and defined size . . . ".
Kim, et al., Biochim. Biophys. Acta, 728:339–348, 1983, "Preparation of multivesicular liposomes".
Kim, et al., Biochim. Biophys. Acta, 793:801, 1985, "Preparation of multilamellar vesicles of defined size–distribution by solvent–spherule . . . ".
Kim, et al., Cancer Treat. Rep., 71:705–711, 1987, "Multivesicular liposomes containing cytarabine entrapped in the presence of . . . ".
Kim, et al., Cancer Research, 47:3935–3937, 1987, "Multivesicular Liposomes Containing cytosine arabinoside for slow–release intrathecal therapy."
Kim, et al., Cancer Treat. Rep., 71:447–450, 1987, "Multivesicular liposomes containing cytosine arabinoside for slow–release . . . ".
Bonetti, et al., Cancer Chemotherapy and Pharmacology, In Press, 1993, "An extended–release formulation of methotrexate for subcutaneous . . . ".
Kim, et al., Cancer Res., 53:1596–1598, 1993, "Prolongation of drug action in CSF by encapsulation into multivesicular liposomes."
Kim, et al., Cancer Chemother Pharmacology, 19:307–310, 1987, "Modulation of the peritoneal clearance of liposomal ara–C by blank liposomes."
Roy, et al., Cancer Chemother, Pharm., 28:105–108, 1991, "Multivesicular liposomes containing bleomycin for subcutaneous administration."

(List continued on next page.)

Primary Examiner—Nathan M. Nutter
Attorney, Agent, or Firm—Fish & Richardson P.C.

[57] ABSTRACT

A method for ameliorating a neurological disorder in a human by administration to the cerebrospinal fluid (CSF) of a therapeutic agent in a dispersion system which allows the therapeutic agent to persist in the cerebro-ventricular space.

5 Claims, 8 Drawing Sheets

OTHER PUBLICATIONS

Kim, et al., Reg. Cancer Treat., 2:170–173, 1989, "Intratumoral chemotherapy with multivesicular liposomes containing 1–b–D–arabino . . . ".

Kim, et al., J. Inf. Dis., 162:750–752, 1990, "Multivesicular liposomes for CSF delivery of retroviral agent DDC."

Chamberlain, et al., Archives of Neurol, 50(3):261–264, 1993, "Treatment of leptomeningeal metastasis with intraventricular administration of . . . ".

Chatelut, et al., Cancer Them. Pharmacol., 32:179–182, 1993, "A slow–release methotrexate formulation for inrathecal chemotherapy."

Russack, et al., Ann. Neurol., 34:108–112, 1993, "Quantitative cerebrospinal fluid cytology in patients receiving intracavitary chemotherapy."

Kim, et al., J. Clin. Oncol., 11:2186–2193, 1993, "Extended cerebrospinal–fluid cytarabine exposure following intrathecal administration of DTC 101."

Kim, Drugs, 46:618–638, 1993, "Liposomes as carriers of cancer chemotherapy: a review."

Kim, Kim, Kim, Cancer Chemother. Pharmacol., 33:187–190, 1993, "Extended–release formulation of morphine for subcutaneous administration."

Ishii, Liposome Technology, 1:111–121, 1993, "Production and Size Control of large unilamellar liposomes by emulsification".

Cullis, et al., Phospholipids and Cellular Regulation, 1:65–123, 1985, "Structural properties and functional roles of phospholipids in . . . ".

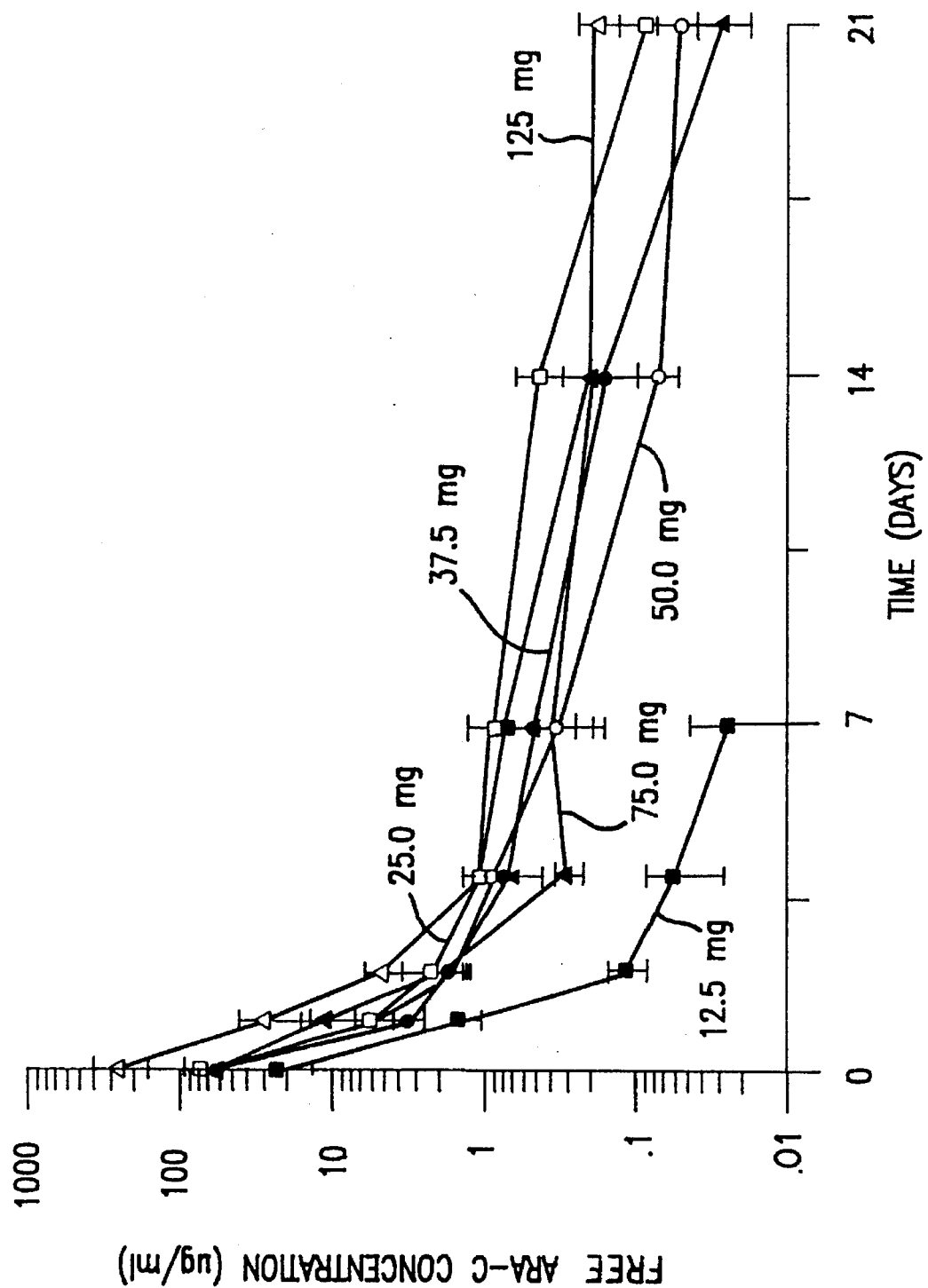

METHOD FOR TREATING NEUROLOGICAL DISORDERS

This is a divisional of application Ser. No. 08/062,799, filed May 14, 1993, U.S. Pat. No. 5,455,044.

BACKGROUND OF THE INVENTION

1. Field of the Invention

The present invention relates to a method for treating a neurological disorder using a slow-release vehicle for delivery of a therapeutic agent to the cerebrospinal fluid (CSF) of a human.

2. Description of the Related Art

Neurological disorders are among the most difficult diseases to treat. A major complicating factor in treating such disorders is the inability of many drugs to penetrate the blood-brain barrier when the agent is administered systemically. This ineffectiveness of classical drug delivery to address this need is particularly problematic with respect to chronic neurological disorders, such as those caused by benign or malignant cell proliferation or various viral etiologic agents.

Among the most difficult chronic neurological disorders to treat are those derived from metastatic infiltration, such as neoplastic meningitis. Neoplastic meningitis results from the metastatic infiltration of the leptomeninges by cancer, and is most commonly a complication of acute leukemia, lymphoma, or carcinoma of the breast and lung. Autopsy studies indicate that 5 to 8 percent of solid tumor patients develop metastasis to the leptomeninges during the course of disease. Evidence suggests that the incidence of neoplastic meningitis may be increasing, in part due to increased survival from effective systemic therapies. (Bleyer, *Curr. Probl. Cancer*, 12:184, 1988).

Standard treatment for neoplastic meningitis includes single agent or combination intrathecal chemotherapy and radiation therapy. Radiotherapy to the entire neuraxis often produces severe marrow depression and has not been satisfactory in controlling active leptomeningeal disease except in leukemic meningitis. (Kogan, in *Principle and Practice of Radiation Oncology*, Perez, et al. eds., Lippincott, Philadelphia, Pa., pp. 1280–1281, 1987). Systemic chemotherapy likewise is not generally effective in active meningeal malignancy because of poor drug penetration through the blood-brain barrier. (Biasberg, et al., *Can. Treat. Rep.*, 61:633, 1977; Shapiro, et eL, *New Eng. J. Med.*, 293:161, 1975). Cytarabine, one of the three chemotherapeutic agents most commonly used for intrathecal therapy of neoplastic meningitis, is a cell-cycle phase specific agent that kills cells only when DNA is being synthesized. Consequently, optimal tumor kill with agents such as cytarabine requires constant infusion or frequent daily injections to maintain therapeutic concentrations for extended periods in CSF. This procedure is uncomfortable for patients, time consuming for physicians, and associated with an increased risk of infectious meningitis. Therefore, there is a need for a slow-releasing depot formulation which can allow a therapeutic agent to persist in contact with a neurological disorder in order to achieve an ameliorative effect. The present invention addresses this need.

SUMMARY OF THE INVENTION

The present invention arose from the seminal discovery that the clinical effectiveness of therapeutic agents in the treatment of neurological disorders in humans could be greatly enhanced if the therapeutic agent was administered as part of a dispersion system. This therapeutic approach allows effective dose levels of the agent to be maintained over a relatively long period of time such that the neurological disorder is continuously exposed to the agent. Surprisingly, the dispersion system containing the therapeutic agent can be effectively administered intralumbar even though the primary foci of the neurological disorder are centered in the cranium region, such as the ventricles.

DETAILED DESCRIPTION OF THE PREFERRED EMBODIMENT

Figure 1A:
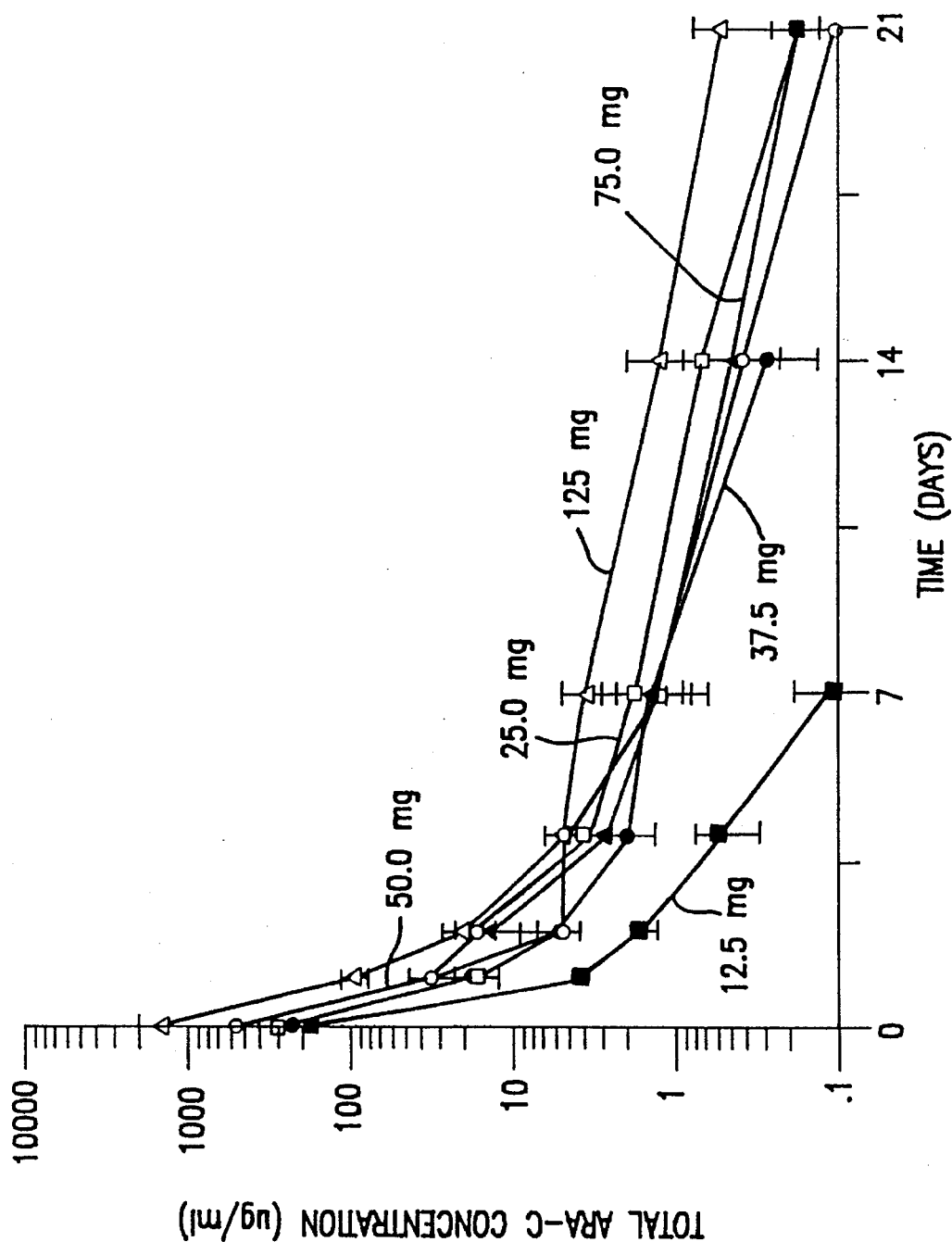
FIG. 1[Panels A+B] shows the ventricular CSF pharmokinetics of intraventricularly administered DTC 101 as a function of dose from 12.5 to 125 mg.

The present invention is directed to a method for ameliorating neurological disorders which comprises administering a therapeutic agent to the cerebral spinal fluid (CSF). The surprising ability of the therapeutic agent to ameliorate the neurological disorder is due to the presentation of the therapeutic agent in a dispersion system which allows the agent to persist in the cerebro-ventricular space. The ability of the method of the invention to allow the therapeutic agent to persist in the region of the neurological disorder provides a particularly effective means for treating those disorders which are chronic and, thereby, are particularly difficult to achieve a clinical effect.

The term "neurological disorder" denotes any disorder which is present in the brain, spinal column, and related tissues, such as the meninges, which are responsive to an appropriate therapeutic agent. Among the various neurological disorders for which the method of the invention is effective are those which relate to a cell proliferative disease. The term "cell proliferative disease" embraces malignant as well as non-malignant cell populations which often appear morphologically to differ from the surrounding tissue. Thus, the cell proliferative disease may be due to a benign or a malignant tumor. In the latter instance, malignant tumors may be further characterized as being primary tumors or metastatic tumors, that is, tumors which have spread from systemic sites. Primary tumors can arise from glial cells (astrocytoma, oligodendroglioma, glioblastoma), ependymal cells (ependymoma) and supporting tissue (meningioma, schwannoma, papilloma of the choroid plexus). In children, tumors typically arise from more primitive cells (medulloblastoma, neuroblastoma, chordoma), whereas in adults astrocytoma and glioblastoma are the most common. However, the most common CNS tumors in general are metastatic, particularly those which infiltrate the leptomeninges. Tumors that commonly metastatically invade the meninges include non-Hodgkin's lymphoma, leukemia, melanoma, and adenocarcinoma of breast, lung, or gastrointestinal origin.

The method of the invention is also useful in ameliorating neurological disorders which arise as a result of an infectious disease. Aseptic meningitis and encephalitis are CNS diseases which are caused by a virus. Among the viral infections which may benefit most from the ability of the method of the invention to allow the therapeutic agent to persist are those viral diseases caused by a slow virus or a retrovirus. Of particular interest among the retroviruses are the Lentivirus, which include HTLV-I, HTLV-II, HIV-1 and HIV-2.

Neurological disorders which arise due to an infectious disease caused by a prokaryote can also be treated according to the method of the invention. Typically, the procaryotic etiologic agent is a bacteria such as *Hemophilus influenzae, Neisseria meningitidis, Streptococcus pneumonia, Pseudomonas aeruginosa, Escherichia coli, Klebsiella-Enterobacter, Proteus, Mycobacterium tuberculosis, Staphylococcus aureus*, and *Listeria monocytogenes*. Alternatively, the infectious disease can be caused by a eukaryote, such as a fungus. Important fungi which can be treated according to the method invention include *Cryptococcus, Coccidioides immitis, Histoplasma, Candida, Nocardia*, and *Blastomyces*.

The therapeutic agents used according to the method of the invention are administered to the CSF in a delivery system such as synthetic or natural polymers in the form of macromolecular complexes, nanocapsules, microspheres, or beads, and lipid-based systems including oil-in-water emulsions, micelles, mixed micelles, synthetic membrane vesicles, and resealed erythrocytes. These systems are known collectively as dispersion systems. Typically, the particles comprising the system are about 20 nm–50 μm in diameter. The size of the particles allows them to be suspended in a pharmaceutical buffer and introduced to the CSF using a syringe. The administration may be intraventricularly or, more preferably, intrathecally. Most preferred is injection of the particles by intralumbar puncture.

Materials used in the preparation of dispersion systems are typically sterilizable via filter sterilization, nontoxic, and biodegradable, for example, albumin, ethylcellulose, casein, gelatin, lecithin, phospholipids, and soybean oil can be used in this manner. Polymeric dispersion systems can be prepared by a process similar to the coacervation of microencapsulation. If desired, the density of the dispersion system can be modified by altering the specific gravity to make the dispersion hyperbaric or hypobadic. For example, the dispersion material can be made more hyperbaric by the addition of iohexol, iodixanol, metrizamide, sucrose, trehalose, glucose, or other biocompatible molecules with high specific gravity.

One type of dispersion system which can be used according to the invention consists of a dispersion of the therapeutic agent in a polymer matrix. The therapeutic agent is released as the polymeric matrix decomposes, or biodegrades, into soluble products which are excreted from the body. Several classes of synthetic polymers, including polyesters (Pitt, et al, in *Controlled Release of Bioactive Materials*, R. Baker, Ed., Academic Press, New York, 1980); polyamides (Sidman, et al., *Journal of Membrane Science*, 7:227, 1979); polyurethanes (Maser, et al., *Journal of Polymer Science, Polymer Symposium*, 66:259, 1979); polyorthoesters (Heller, et al., *Polymer Engineering Science*, 21:727, 1981); and polyanhydrides (Leong, et aL, *Biomaterials*, 7:364, 1986) have been studied for this purpose. Considerable research has been done on the polyesters of PLA and PLA/PGA. Undoubtedly, this is a consequence of convenience and safety considerations. These polymers are readily available, since they have been used as biodegradable sutures, and they decompose into non-toxic lactic and glycolic acids (see, U.S. Pat. Nos. 4,578,384; U.S. Pat. No. 4,765,973; incorporated by reference).

Solid polymeric dispersion systems can be synthesized using such polymerization methods as bulk polymerization, interfacial polymerization, solution polymerization, and ring opening polymerization (Odian, G., *Principles of Polymerization*, 2nd ed., John Wiley & Sons, New York, 1981). Using any of these methods, a variety of different synthetic polymers having a broad range of mechanical, chemical, and biodegradable properties are obtained; the differences in properties and characteristics are controlled by varying the parameters of reaction temperatures, reactant concentrations, types of solvent, and reaction time. If desired, the solid polymeric dispersion system can be produced initially as a larger mass which is then ground, or otherwise processed, into particles small enough to maintain a dispersion in the appropriate physiologic buffer (see, for example, U.S. Pat. No. 4,389,330; U.S. Pat. No. 4,696,258; incorporated by reference).

The mechanism of release of therapeutic agent from biodegradable slabs, cylinders, and spheres has been described by Hopfenberg (in *Controlled Release Polymeric Formulations*, pp. 26–32, Paul, D. R. and Harris, F. W., Eds., American Chemical Society, Washington, D.C., 1976). A simple expression describing additive release from these devices where release is controlled primarily by matrix degradation is:

$$M_t/M_{2\infty}=1-[1-k_0t/C_0a]^n$$

where n=3 for a sphere, n=2 for a cylinder, and n=1 for a slab. The symbol a represents the radius of a sphere or cylinder or the half-thickness of a slab. $M_t$ and $M_\infty$ are the masses of drug release at time t and at infinity, respectively.

Most preferred as a dispersion system according to the invention are synthetic membrane vesicles. The term "synthetic membrane vesicles" denotes structures having one or more concentric chambers, commonly known as liposomes, as well as structures having multiple non-concentric chambers bounded by a single bilayer membrane.

When phospholipids are dispersed in aqueous media, they swell, hydrate, and spontaneously form muitilamellar concentric bilayer vesicles with layers of aqueous media separating the lipid bilayer. Such systems are usually referred to as muitilamellar liposomes or multitamellar vesicles (MLVs) and have diameters ranging from about 100 nm to about 4 μm. When MLV's are sonicated, small unilamellar vesicles (SUVs) with diameters in the range of from about 20 nm to about 50 nm are formed, which contain an aqueous solution in the core of the SUV.

The composition of the synthetic membrane vesicle is usually a combination of phospholipids, particularly high-phase-transition-temperature phospholipids, usually in combination with steroids, especially cholesterol. Other phospholipids or other lipids may also be used.

Examples of lipids useful in synthetic membrane vesicle production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and are saturated. Illustrative phospholipids include egg phosphatidylcholine, dipalmitoylphosphatidylcholine, and distearoylphosphatidyl-choline.

In preparing vesicles containing a therapeutic agent, such variables as the efficiency of drug encapsulation, lability of the drug, homogeneity and size of the resulting population of vesicles, drug-to-lipid ratio, permeability instability of the preparation, and pharmaceutical acceptability of the formulation should be considered. (Szoka, et al., *Annual Reviews of Biophysics and Bioengineering,* 9:467, 1980; Deamer, et aL., in Liposomes, Marcel Dekker, New York, 1983, 27; Hope, et al., *Chem. Phys. Lipids,* 40:89, 1986).

If desired, it is possible to produce synthetic membrane vesicles with various degrees of target specificity. The targeting of vesicles has been classified based on anatomical and mechanistic factors. Anatomical classification is based on the level of selectivity, for example, organ-specific, cell-specific, and organelle-specific. Mechanistic targeting can be further distinguished based upon whether it is passive or active. Passive targeting utilizes the natural tendency of vesicles to distribute to cells of the reticulo-endothelial system (RES) in organs which contain sinusoidal capillaries. Active targeting, on the other hand, involves the alteration of the vesicle by coupling the vesicle to a specific ligand such as a monoclonal antibody, sugar, glycolipid, or protein, or by changing the composition or size of the vesicles in order to achieve targeting to organs and cell types other than the naturally occurring sites of localization. Alternatively, vesicles may physically localize in capillary beds.

Another dispersion system which can be used according to the invention is resealed erythrocytes. When erythrocytes are suspended in a hypotonic medium, swelling occurs and the cell membrane ruptures. As a consequence, pores are formed with diameters of approximately 200–500 Å which allow equilibration of the intracellular and extracellular environment. If the ionic strength of this surrounding media is then adjusted to isotonic conditions and the cells incubated at 37° C., the pores will close such that the erythrocyte reseals. This technique can be utilized to entrap the therapeutic agent inside the resealed erythrocyte.

The surface of the dispersion system may be modified in a variety of ways. Non-lipid material may be conjugated via a linking group to one or more hydro-phobic groups, for example, alkyl chains from about 12–20 carbon atoms. In the case of a synthetic membrane vesicle delivery system, lipid groups can be incorporated into the lipid bilayer in order to maintain the compound in stabile association with the membrane bilayer. Various linking groups can then be used for joining the lipid chains to the compound.

Whether a ligand or a receptor, the number of molecules bound to a synthetic membrane vesicle will vary with the size of the vesicle, as well as the size of the molecule to be bound, the binding affinity of the molecule to the target cell receptor or ligand, as the case may be, and the like. In most instances, the bound molecules will be present on the vesicle from about 0.05 to about 2 mol %, preferably from about 0.1 to about 1 mol %, based on the percent of bound molecules to the total number of molecules in the outer membrane bilayer of the vesicle.

In general, the compounds to be bound to the surface of the targeted delivery system will be ligands and receptors Which will allow the dispersion system to actively "home in" on the desired tissue. A ligand may be any compound of interest which will specifically bind to another compound, referred to as a receptor, such that the ligand and receptor form a homologous pair. The compounds bound to the service of the dispersion system may vary from small haptens from about 125–200 molecular weight to much larger antigens with molecular weights of at least about 6000, but generally of less than 1 million molecular weight. Proteinaceous ligands and receptors are of particular interest. In general, the surface membrane proteins which bind to specific effector molecules are referred to as receptors. As presently used, however, most receptors will be antibodies. These antibodies may be monoclonal or polyclonal and may be fragments thereof such as Fab, $F(ab')_2$, and $F_v$, which are capable of binding to an epitopic determinant. Techniques for binding of proteins, such as antibodies, to synthetic membrane vesicles are well known (see, for example, U.S. Pat. No. 4,806,466, incorporated by reference).

The term "therapeutic agent" as used herein for the compositions of the invention includes, without limitation, drugs, radioisotopes, and immunomodulators. Similar substances are known or can be readily ascertained by one of skill in the art. There may be certain combinations of therapeutic agent with a given type of dispersion system which are more compatible than others. For example, the method for producing a solid polymeric dispersion may not be compatible with the continued biological activity of a proteinaceous therapeutic agent. However, since conditions which would produce an uncompatible pairing of a particular therapeutic agent with a particular dispersion system are well known, or easily ascertained, it is a matter of routine to avoid such potential problems.

The drugs which can be incorporated in the dispersion system include non-proteinaceous as well as proteinaceous drugs. The term "non-proteinaceous drugs" encompasses compounds which are classically referred to as drugs such as, for example, mitomycin C, daunorubicin, vinblastine, AZT, and hormones. Of particular interest are anti-tumor cell-cycle specific drugs such as cytarabine, methotrexate, 5-fluorouracil (5-FU), floxuridine (FUDR), bleomycin, 6-mercapto-purine, 6-thioguanine, fludarabine phosphate, vincristine, and vinblastine. Similar substances which can also be used according to the invention are within the skill of the art.

The proteinaceous drugs which can be incorporated in the dispersion system include immunomodulators and other biological response modifiers as well as antibodies. The term "biological response modifiers" encompasses substances which are involved in modifying the immune response in such manner as to enhance the particular desired therapeutic effect, for example, the destruction of tumor cells. Examples of immune response modifiers include such compounds as lymphokines. Examples of lymphokines include tumor necrosis factor, the interleukins, lymphotoxin, macrophage activating factor, migration inhibition factor, colony stimulating factors and the interferons. Interferons which can be incorporated into the dispersion systems include α-interferon, β-interferon, and γ-interferon and their subtypes. In addition, peptide or polysaccharide fragments derived from these proteinaceous drugs, or independently, can also be incorporated. Those of skill in the art will know, or can readily ascertain, other substances which can act as proteinaceous drugs.

In using radioisotopes to treat cell proliferative disorders, such as tumors, certain radioisotopes may be more preferable than others depending on such factors, for example, as tumor distribution and mass, as well as isotope stability and emission. Depending on the type of malignancy present some emitters may be preferable to others. In general, α and β particle-emitting radioisotopes are preferred in immunotherapy. For example, if a patient has solid tumor foci a high energy β emitter capable of penetrating several millimeters of tissue, such as $^{90}Y$, may be preferable. On the other hand, if the malignancy consists of single target cells, as in the case of leukemia, a short range, high energy α emitter such as $^{212}$Bi may be preferred. Examples of radioisotopes which can be incorporated in the dispersion system for therapeutic purposes are $^{125}$I, $^{131}$I, $^{90}$Y, $^{67}$Cu, $^{212}$Bi, $^{211}$At, $^{212}$Pb, $^{47}$Sc, $^{109}$Pd and $^{188}$Re. Other radioisotopes which can be incorporated are within the skill in the art.

When an antibody is incorporated into the dispersion system, the antibody, whether monoclonal or polyclonal, may be unlabeled or labeled with a therapeutic agent. The term "antibody" or "immunoglobulin" as used herein, includes intact molecules as well as fragments thereof, such as Fab, F(ab')$_2$, and F$_v$, which are capable of binding to an epitopic determinant on a cell proliferative or infectious neurological disorder etiologic agent. When coupled to an antibody, the therapeutic agent can be coupled either directly or indirectly. One example of indirect coupling is by use of a spacer moiety. These spacer moieties, in turn, can be either insoluble or soluble (Diener, et al., *Science*, 231:148, 1986) and can be selected to enable drug release from the antibody molecule at the target site. Examples of therapeutic agents which can be coupled to the antibody for immunotherapy are drugs and radioisotopes, as described above, as well as lectins and toxins.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an α and β subunit which under proper conditions can be separated. The toxic α component can be bound to an antibody and used for site specific delivery to a target cell for which the antibodies are specific. Other therapeutic agents which can be coupled to the monoclonal antibodies are known, or can be easily ascertained, by those of ordinary skill in the art.

The labeled or unlabeled antibodies can also be used in combination with other therapeutic agents such as those described above. Especially preferred are therapeutic combinations comprising a monoclonal antibody and an immunomodulator or other biological response modifier. Thus, for example, a monoclonal antibody can be used in combination with α-interferon. This treatment modality enhances monoclonal antibody targeting of carcinomas by increasing the expression of monoclonal antibody reactive antigen by the carcinoma cells (Greiner, et al., *Science,* 235:895, 1987). A dispersion system based on the use of a synthetic membrane vesicle with multiple non-concentric chambers is particularly useful with combination therapy, since the non-concentric chambers can be loaded with different therapeutic agents. Those of skill in the art will be able to select from the various biological response modifiers to create a desired effector function which enhances the efficacy of the monoclonal antibody or other therapeutic agent used in combination.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the neurological disorder, the condition of the patient and half-life of the agent.

The term "therapeutically effective" as it pertains to the compositions of the invention means that the therapeutic agent is present at a concentration sufficient to achieve a particular medical effect for which the therapeutic agent is intended. Examples, without limitation, of desirable medical effects which can be attained are chemotherapy, antibiotic therapy, and regulation of metabolism. Exact dosages will vary depending upon such factors as the particular therapeutic agent and desirsable medical effect, as well as patient factors such as age, sex, general condition and the like. Those of skill in the art can readily take these factors into account and use them to establish effective therapeutic concentrations without resort to undue experimentation.

The foregoing is meant to illustrate, but not to limit, the scope of the invention. Indeed, those of ordinary skill in the art can readily envision and produce further embodiments, based on the teachings herein, without undue experimentation.

EXAMPLE 1

PRODUCTION OF DEPO/ARA-C (DTC101)

This example describes the production of a synthetic membrane vesicle having multiple non-concentric chambers containing ara-C which are bounded by a single bilayer membrane.

Dioleoyl lecithin (8.3 g), dipalmitoylphosphatidyl glycerol (1.66 g), cholesterol (6.15 g), and triolein (1.73 g) were mixed with 800 ml of chloroform (the lipid phase) in a 13-liter glass homogenizer vessel fitted with a 2-inch mixing blade. Next, Cytosine arabinoside (33 mg/ml) was dissolved in 0.151 N HCl (at a final volume of 1.2 liters) and added to the homogenizer vessel. To form a water-in-oil emulsin, the mixing blade was rotated at 8000 rpm for 10 minutes.

Low ionic strength aqueous component comprising free base lysine (40 mM) and glucose (3.2%) was added to the homogenizer to form the chloroform spherules and the mixing blade was rotated at 3500 rpm for 90 seconds. To remove the chloroform, nitrogen gas was bubbled through the mixture at 62 liters per minute for 30 minutes while the vessel was heated to 35 ° C. The resulting product was purified and concentrated by diafiltration using polysulfone hollow-fiber with 0. 1μ pore size and 8 $ft^2$ surface area.

EXAMPLE 2

INTRATHECAL AND INTRAVENTRICULAR TREATMENT WITH

ENCAPSULATED DEPO/ARA-C

A. PATIENTS AND METHODS

Twelve patients with a histologically proven diagnosis of cancer and radiological or cytologic evidence of neoplastic meningitis were treated. This human investigation was performed after approval by the UCSD Human Subjects Committee. There was no performance status requirement and prior intra-CSF chemotherapy was allowed. The patients were given 47 total doses of DTC 101. There were 4 patients with hematological malignancies and 8 with solid tumors (TABLE 1). Concurrent systemic chemotherapy was given to 5 patients.

TABLE 1

PATIENT CHARACTERISTICS

| | |
|---|---|
| Total Number of Patients | 12 |
| Male | 7 |
| Female | 5 |
| Ages (range, years) | 6–73 |
| Median | 38 |
| Diagnoses | |
| Chronic myelogenous leukemia in blast crisis | 1 |
| AIDS-related non-Hodgkin's lymphoma | 2 |
| Multiple myeloma | 1 |
| Breast cancer | 2 |
| Non-small cell lung cancer | 1 |
| Head and neck cancer | 1 |
| Renal cell tumor | |
| Melanoma | |
| Primitive neuroectodermal tumor | 2 |
| Prior Therapy for Meningeal Disease | |
| With prior therapy | 9 |
| Without prior therapy | 4 |
| Types of Prior Therapy | |
| Methotrexate | 6 |
| Cyatarabin | 3 |
| ThioTEPA | 3 |
| Interferon | 1 |

An Ommaya reservoir was placed in the right lateral ventricle in all but one patient with chronic myelogenous leukemia in blast crisis. Therapy consisted of DTC 101 suspended in a preservative-free 0.9% NaCl solution administered intraventricularly or by the lumbar intrathecal route as a single injection once every 2–3 weeks. The reservoir was flushed with autologous CSF after DTC 101 dosing and at each CSF sampling.

B. TREATMENT

The initial dose of 12.5 mg was escalated (25, 37.5, 50, 75, 125 mg) after at least 3 cycles in 2 patients who were available for evaluation. Treatment was continued until disease progression or to a maximum of 7 doses. Initial work-up included history and physical examination and complete neurological examination; CBC and platelet count; CSF sample for cytology; serum chemistries; CT or MR brain scan with and without appropriate contrast agents and Indium-DTPA CSF flow studies (Chamberlain, et al., *Neurol.*, 40:435–438, 15 1990; Chamberlain, et al., *Neurol.*, 41:1765–1769, 1991). Before each cycle of DTC 101. complete neurological history and examination, blood counts, and chemistries were done, and CSF samples were obtained for cytologic examination. Complete cytologic response was defined as two consecutive negative CSF cytology examinations at least one week apart; anything less than a complete response was considered as no response. Progressive disease was defined as conversion from negative to positive cytology. Changes in parenchymal CNS lesions or lesions outside the CNS were not used as part of response determination since these were not expected to be influenced by intra-CSR therapy. Treatment-induced toxicities were scored using the "Common Toxicity Scale" of the National Cancer Institute.

FIG. 1 shows the CSF pharmacokinetics of cytarabine following intraventricular administrations of DTC 101 at various doses ranging from 12.5 to 125 mg, where CSF samples were obtained from the same ventricle into which DTC 101 had been injected. Panel A, total cytarabine concentration; panel B, free cytarabine concentration. Each data point is an average from at least three courses and the error bars represent standard errors of mean. Following intraventricular administration of a maximum tolerated dose (75 mg), the ventricular concentration of free cytarabine (cytarabine that had been released from DepoFoam particles into the CSF) decreased biexponentially with an average initial ($\alpha$) half-life of 9.4±1.6 hrs (SEM), and terminal $\beta$) half-life of 141 ±23 hrs (SEM). The total ventricular concentration (free plus encapsulated cytarabine) decreased in a similar biexponential manner.

Pharmacokinetic Studies

Ventricular CSF and blood samples were obtained immediately before injection and at 1 hr and then 1, 2, 4, 7, 14, and 21 days following injection. Lumbar CSF samples were obtained in selected patients as a part of evaluation for lumbar CSF cytology at one of these same time points. For intralumbar injections, a sample from the lumbar sac was obtained 3 minutes after injection in lieu of the 1 hr sample. All CSF and blood samples were collected in tubes containing tetrahydrouridine at a final concentration of 40 µM to prevent in vitro catabolism of cytarabine to uracil arabinoside (ara-U) by cytidine deaminase. The heparinized blood samples were immediately placed on ice and plasma was separated from blood cells by centrifugation. The CSF samples were centrifuged at 600 X g for 5 minutes to separate DepoFoam particles from the free cytarabine fraction (the supernate). The DepoFoam pellet was lysed by vortexing sequentially in 200 µl methanol and in distilled water. The free cytarabine fractions of CSF were analyzed without further processing. The plasma was ultrafiltered (YMT membrane, No. 4104; Areicon Corp., Danvers, Mass.). The CSF and plasma samples were stored frozen at −20° until analysis by a modification of previously described method (Kaplan, JG, et al., *J Neuro-Onc*, 9:225–229, 1990). The samples were analyzed on a high performance liquid chromatography system (Waters Associates, Milford, Mass.) with 254 and 280 mm UV detectors, two Pecosphere C-18 reverse-phase columns (3X3C Cartridge; Perkin-Elmer, Norwalk, Conn.) in tandem, and 6.7 mM potassium phosphate/3.3 mM phosphoric acid mixture (pH 2.8) as an isocratic mobile phase at a flow rate of 1.0 ml/min. Retention time for cytarabine was 6 minutes and that for the major metabolite, ara-U, was 7 minutes. There were no interfering peaks.

The pharmacokinetic curves were fit to the biexponential function $C(t)=Ae^{-\alpha t}+Be^{-\beta t}$, where C(t) is the concentration at time 5, A and B are constants and $\alpha$ and $\beta$ are the initial and terminal rate constants. The RSTRIP program (MicroMath Scientific Software, Salt Lake City, Utah) was used to perform the curve fitting by iterative non-linear regression. The area under the concentration-versus-time curve (AUC) was determined by the linear trapezoidal rule up to the last measured concentration and extrapolated to infinity. CSR clearance of cytarabine was determined by dividing the dose of cytarabine by the AUC. The initial volume of distribution of cytarabine in CSF ($V_d$) was calculated by dividing the dose of cytarabine by the concentration measured at 1 hr.

TABLE 2 shows the detailed pharamcokinetic parameters as a function of dose. The half-lives ($T_{1/2}$), volumes of distribution ($V_d$), and clearances (Cl) did not change significantly as the dose was escalated from 12.5 to 125 mg.

TABLE 2

PHARMACOKINETIC PARAMETERS AS A FUNCTION OF DOSE

| Dose | 12.5 mg | 25 mg | 37.5 mg | 50 mg | 75 mg | 125 mg |
|---|---|---|---|---|---|---|
| Cycles | 3 | 6 | 5 | 6 | 7 | 3 |
| Total Cytarabine | | | | | | |
| $C_{max}$ (mg/ml) | 161 ± 35 | 263 ± 51 | 308 ± 98 | 468 ± 112 | 554 ± 146 | 1373 ± 740 |
| $\alpha T_{1/2}$ (hr) | 2.3 ± 5 | 8.0 ± 1.5 | 6.0 ± 1.7 | 5.0 ± 1.0 | 7.6 ± 1.5 | 8.4 ± 1.5 |
| $\beta T_{1/2}$ (hr) | 47 ± 22 | 229 ± 70 | 75 ± 16 | 87 ± 15 | 95 ± 16 | 161 ± 75 |
| AUC (µg-hr/ml) | 2210 ± 452 | 5910 ± 1550 | 4820 ± 1230 | 7390 ± 1150 | 9090 ± 1750 | 20800 ± 9400 |
| Cl (ml/min) | .11 ± .02 | .09 ± .02 | .18 ± .04 | .13 ± .02 | .27 ± .07 | .18 ± /07 |
| $V_d$ (ml) | 91 ± 21 | 112 ± 22 | 206 ± 64 | 150 ± 35 | 275 ± 95 | 286 ± 154 |
| Free Cytarabine | | | | | | |
| $C_{max}$ (mg/ml) | 25 ± 12 | 77 ± 17 | 55 ± 12 | 73 ± 11 | 66 ± 31 | 282 ± 111 |
| $\alpha T_{1/2}$ (hr) | 5.5 ± 7 | 7.6 ± 1.6 | 4.6 ± 1.4 | 5.5 ± 1.4 | 9.4 ± 1.6 | 7.3 ± .1 |
| $\beta T_{1/2}$ (hr) | 71 ± 13 | 123 ± 22 | 112 ± 31 | 80 ± 18 | 141 ± 23 | 129 ± 46 |
| AUC (µg-hr/ml) | 355 ± 151 | −1595 ± 234 | 853 ± 210 | 1327 ± 135 | 1343 ± 465 | 4525 ± 1775 |
| Cl (ml/min) | 1.2 ± .6 | .30 ± .1 | 1.1 ± .3 | .66 ± .06 | 1.7 ± .4 | .73 ± .25 |

Figure 2A:
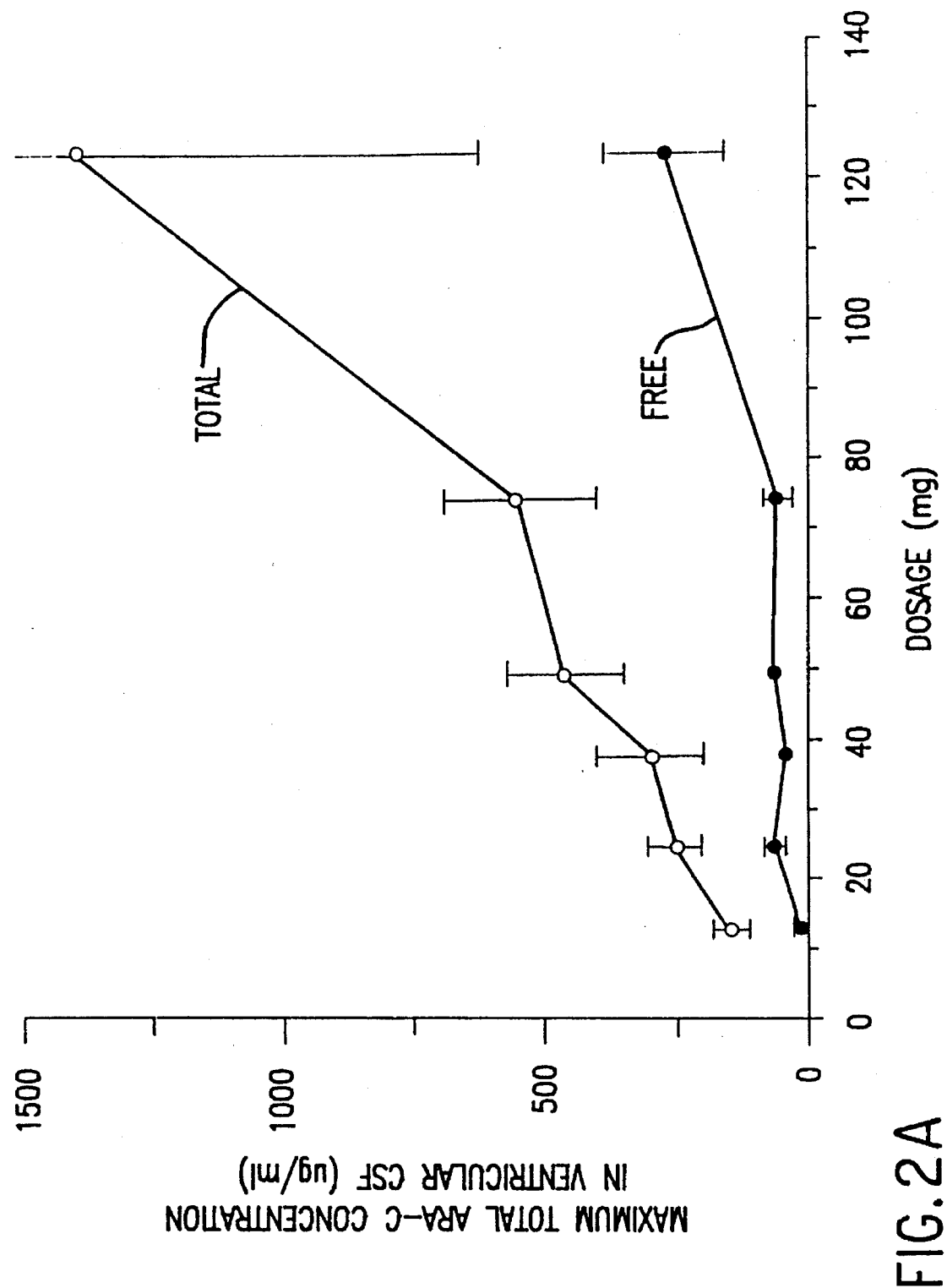
FIGS. 2A and 2B show the maximum CSF cytarabine concentration [Panel A] and AUC [Panel B] as functions of dose.
Figure 2B:
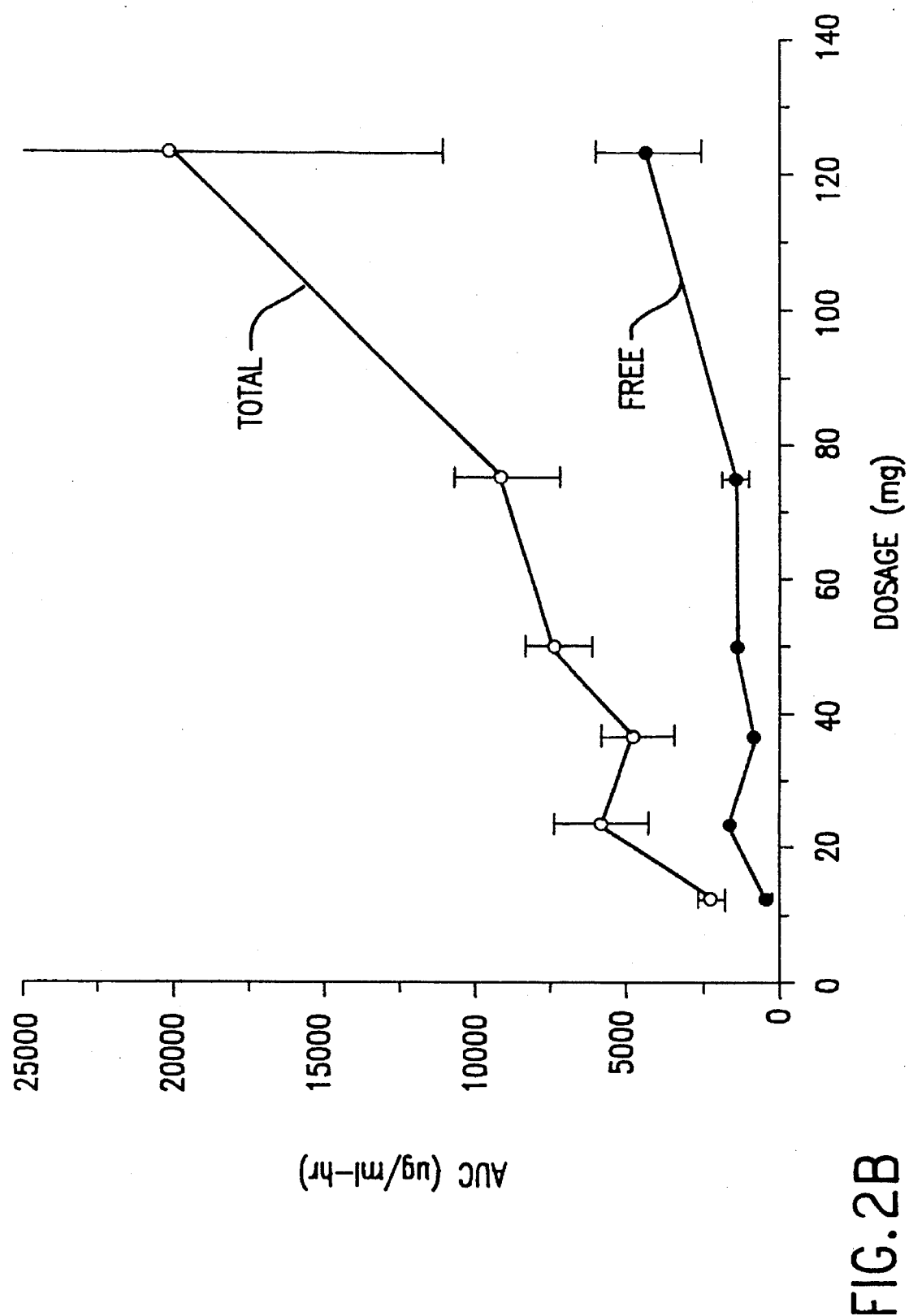

Abbreviations:
$C_{max}$, maximum concentration;
$\alpha T_{1/2}$, initial half-life;
$\beta T_{1/2}$, terminal half-life;
AUC, area under the curve;
Cl, clearance;
$V_d$, volume of distribution FIG. 2 depicts the maximum ventricular cytarabine concentration (Panel A) measured at 1 hr following DTC 101 administration, and the CSF drug exposure (AUC, Panel B) as a function of dose administered intraventricularly. Open and closed circles represent total and free cytarabine, respectively. Each data point is an average from at least three courses nd the error bars represent standard errors of mean. There was a linear relationship between these pharmacokinetic parameters and dose, indicating that there was no saturation of clearance process over the dose range examined. The total ara-U AUC averaged 3.7±0.9% (SEM) of the total cytarabine AUC in the CSF. No cytarabine or ara-U was detected in the plasma (detection limit=0.25 µg/ml for both) at any time point.

Figure 3A:
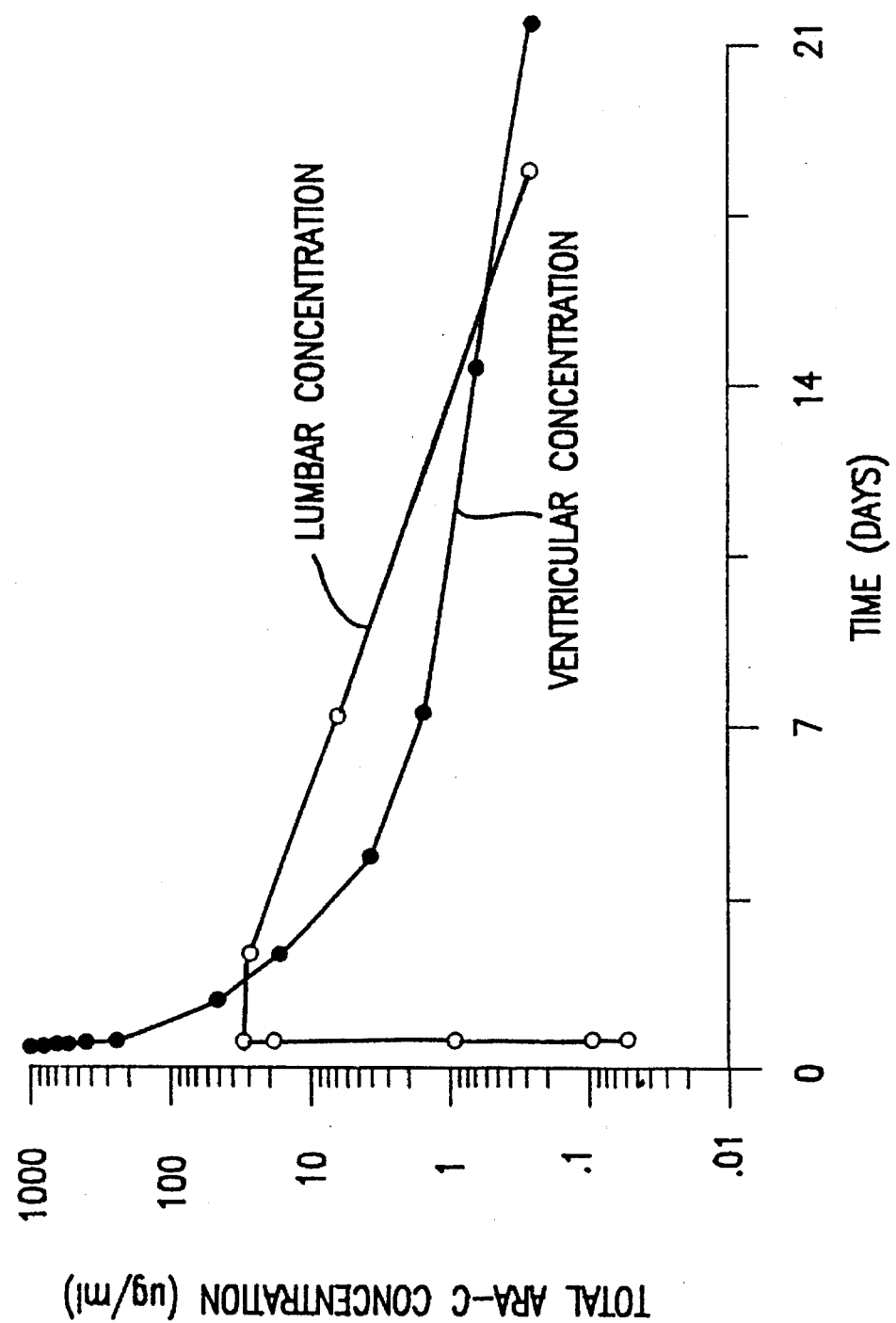
FIGS. 3A through 3C show a comparison of the ventricular (closed circles) and lumbar (open circles) cytarabine concentrations [total and free, Panels A and B, respectively] and DTC 101 particle count [Panel C] as functions of time following intraventricular administration of DTC 101.
Figure 3B:
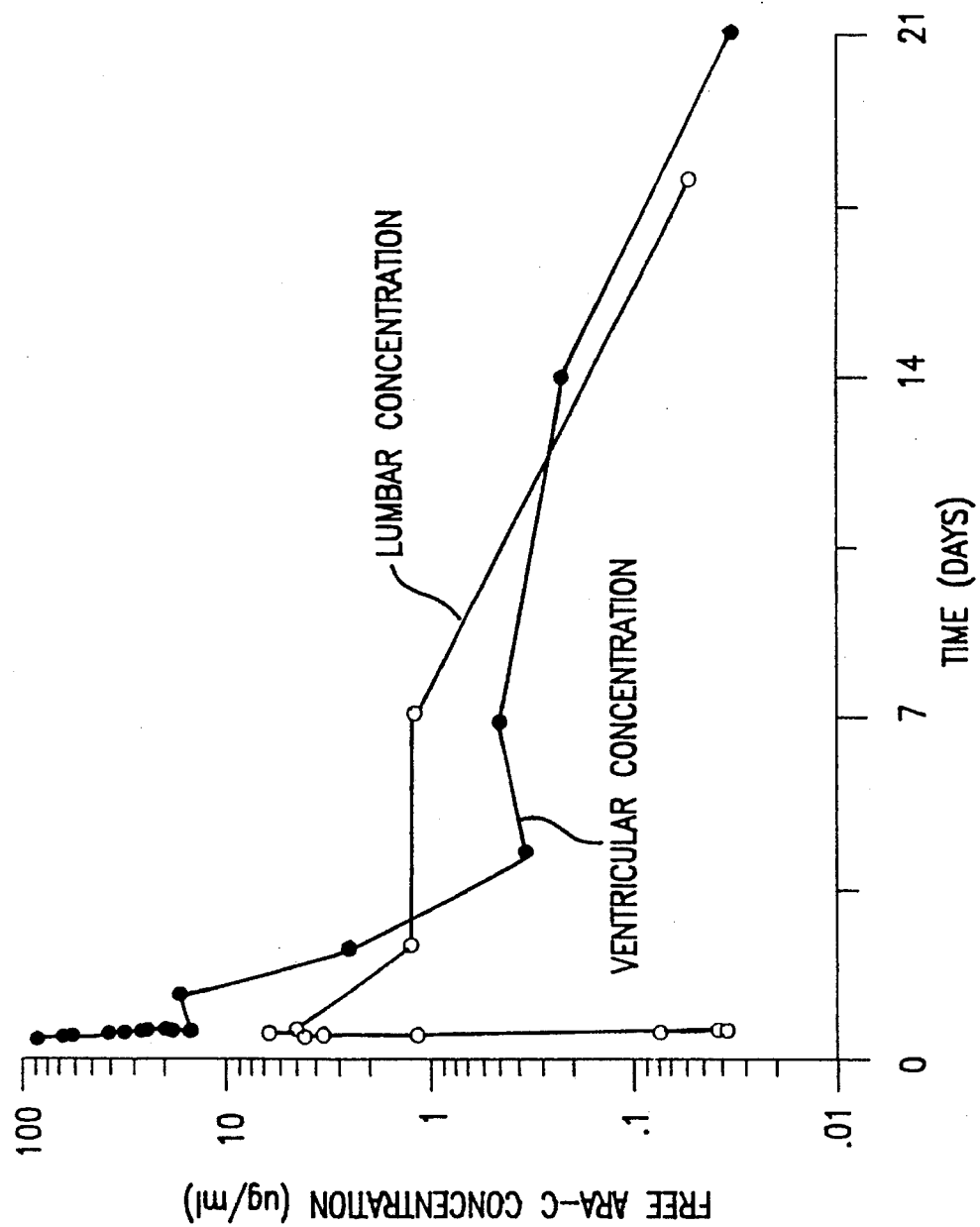
Figure 3C:
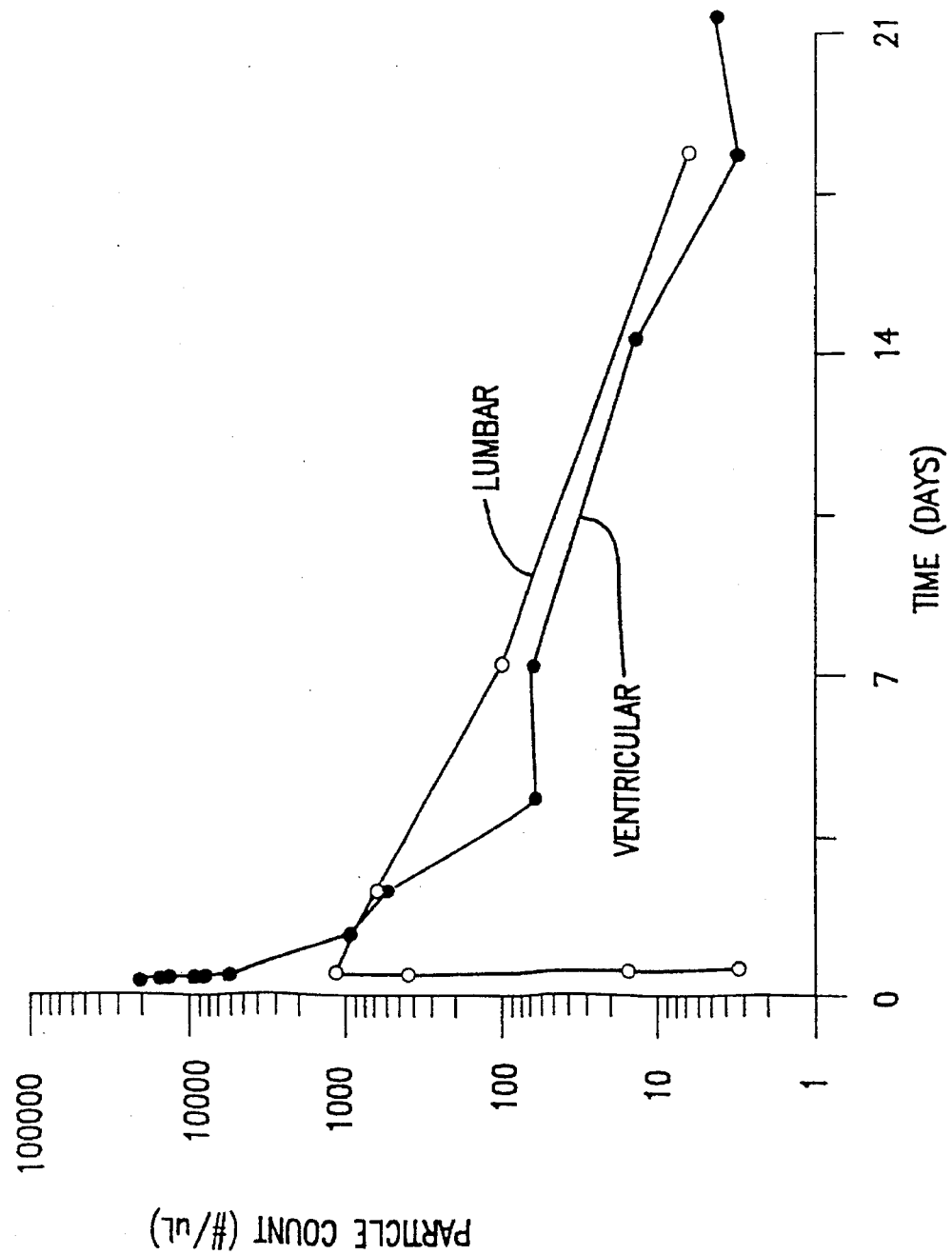

Lumbar CSF samples were obtained during five courses in two patients following intraventricular administration of DTC 101 at the maximum tolerated dose (75 mg). FIG. 3 compares the ventricular drug concentration and DTC 101 particle count with that in the lumbar subarachnoid space. Comparison of the ventricular (closed circles) and lumbar (open circles) cytarabine concentrations (total and free, Panels A and B, respectively) and DTC 101 particle count (Panel C) as functions of time following intraventricular administration of DTC 101. The initial ventricular free cytarabine concentration decreased in an exponential fashion with a half-life of 6.8 hrs; cytarabine became detectable in lumbar CSF at 1.25 hrs and then increased rapidly with a doubling time of 0.53 hrs. Subsequently, the lumbar and ventricular concentrations of free and total cytarabine decreased in parallel fashion, with the lumbar drug concentrations remaining comparable to those in the ventricle throughout the terminal phase of the decay curve.

Figure 4:
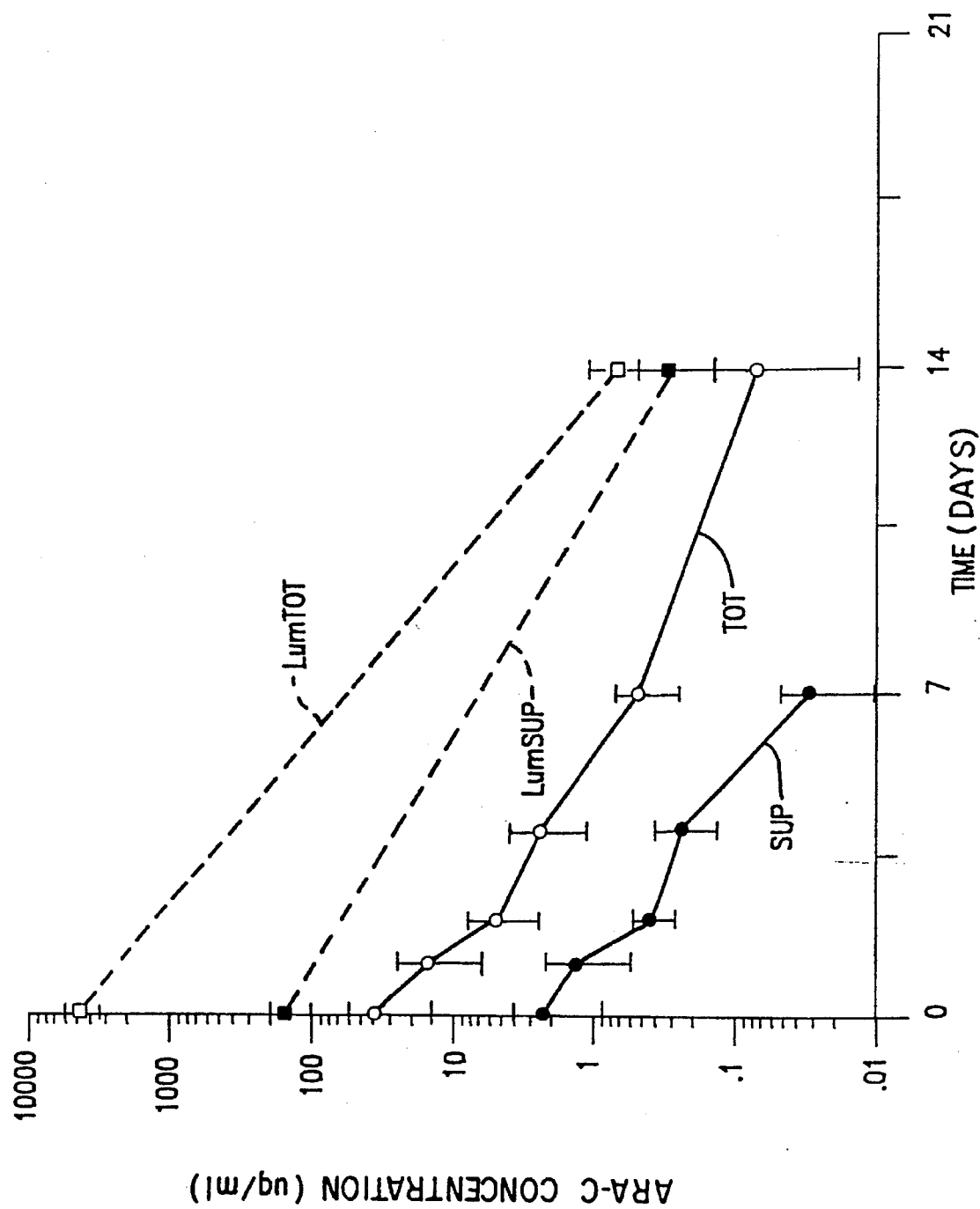
FIG. 4 shows cytarabine concentration in the ventricular CSF as a function of time (solid lines). and lumbar CSF cytarabine concentration at 3 minutes and 14 days (broken lines). following intralumbar administration of DTC 101.

Both ventricular and intralumbar CSF samples were obtained from four patients given DTC 101 intrathecally by lumbar puncture. FIG. 4 shows that a therapeutic concentration of free cytarabine (>0.1 µg/ml) was maintained for 3 to 6 days in ventricular CSF following intrathecal lumbar injection, and a significant concentration of total cytarabine was found in the ventricular CSF for 14 days following intralumbar administration. Cytarabine concentration in the ventricular CSF as a function of time (solid lines), and lumbar CSF cytarabine concentration at 3 minutes and 14-days (broken lines), following intralumbar administration of DTC 101. Open squares and circles represent total cytarabine concentrations and closed squares and circles represent free cytarabine concentrations. A therapeutic concentration of free cytarabine was maintained for more than 14 days in the lumbar subarachnoid space following intralumbar injection.

TABLE 3 summarizes the toxicities of DTC 101 as a function of dose. The toxicities were transient and in no instance did drug-related toxicity delay therapy with a subsequent dose of DTC 101. There was one death due to the occurrence of a toxic enceahalopathy that developed 36 hours following intraventricular administration of 125 mg of DTC 101. This patient was also receiving concurrent whole brain irradiation (20 Gy in 5 fractions) for partial blockage of CSF flow at the base of brain. There were no hematological toxicities attributable to DTC 101 except in one patient who had an autologous bone-marrow transplant two months prior to DTC 101 administration. The maximum tolerated dose of DTC 101 was 75 mg; dose limiting toxicity occurred a dose of 125 mg, at which there was excessive vomiting and encephalopathy (TABLE 3).

TABLE 3

TOXICITY OF DTC 101 AS A FUNCTION OF DOSE

| Dose (mg) | 12.5 | 25 | 37.5 | 50 | 75 | 125 |
|---|---|---|---|---|---|---|
| Patients | 2 | 6 | 5 | 4 | 8 | 4 |
| Courses | 3 | 7 | 7 | 6 | 20 | 4 |
| Fever | 1 (1)* | 0 (4) | 0 (1) | 0 (3) | 0 (5) | 0 (1) |
| Headache | 0 (1) | 0 (7) | 0 (2) | 2 (2) | 0 (4) | 1 (2) |
| Neck/back pain | 0 (0) | 0 (0) | 0 (0) | 0 (1) | 0 (3) | 0 (0) |

TABLE 3-continued

TOXICITY OF DTC 101 AS A FUNCTION OF DOSE

| | | | | | | |
|---|---|---|---|---|---|---|
| Nausea/vomiting | 0 (3) | 1 (2) | 1 (3) | 0 (4) | 2 (4) | 3 (1) |
| Cerebellar | 0 (1) | 0 (0) | 0 (0) | 0 (0) | 0 (0) | 0 (0) |
| Tinnitus | 0 (0) | 0 (1) | 0 (0) | 0 (0) | 0 (0) | 0 (0) |
| Encephalopathy | 0 (0) | 1 (1) | 0 (0) | 1 (0) | 0 (0) | 1 (1) |
| Hyponatremia | 0 (0) | 0 (0) | 0 (0) | 0 (0) | 0 (1) | 0 (0) |

*The numbers in the columns represent toxicities greater than grade 2. The numbers in parenthesis represent toxicities of grade 1 or 2.

TABLE 4 shows that oral dexamethasone in doses of 2 to 4 mg twice per day had a major effect on blunting toxicities associated with DTC 101. Fever, headache, and nausea/vomiting were all reduced. There were three patients who received the same doze of DTC 101 with and without oral dexamethasone.

All three patients manifested toxicity without dexamethasone and in each patient the toxicity was almost completely suppressed with concurrent oral dexamethasone.

TABLE 4

EFFECT OF CONCURRENT ORAL DEXAMETHASONE ADMINISTRATION ON DTC 101 TOXICITY

| | (−) Dexamethasone- 9 | | (+) Dexamethasone 12 | |
|---|---|---|---|---|
| Number of courses | | | | |
| % with toxcity grade | 1–2 | 3–4 | 1–2 | 3–4 |
| Fever | 44 | 0 | 8 | 0 |
| Headache | 44 | 0 | 8 | 0 |
| Back/neck pain | 33 | 0 | 0 | 0 |
| Nausea/vomiting | 22 | 22 | 17 | 8 |
| Encephalopathy | 0 | 0 | 0 | 0 |

Intraventricular and intralumbar routes were combined.

Four patients were treated with DTC 101 by the lumbar intrathecal route, The toxicities were similar to those observed following intraventricular administration except 4 of 9 cycles were associated with grade 1 to 2 low back pain.

Nine of 12 patients had a positive CSF cytology immediately prior to treatment. Seven of these 9 cytologically evaluable patients cleared their CSF of malignant cells with DTC 101 treatment (TABLE 5). The duration of response ranged from 2 to 26 weeks with a median of 16 weeks. One non-responding patient had an AIDS-related non-Hodgkin's lymphoma and the other had a primary brain tumor. Survival time for all patients on study ranged from 3 to 64 weeks (median: 21 weeks).

TABLE 5

CSF CYTOLOGIC RESPONSE TO DTC 101

| | |
|---|---|
| Number of Patients | 12 |
| Number with positive CSF cytology | 9 |

TABLE 5-continued

CSF CYTOLOGIC RESPONSE TO DTC 101

| | |
|---|---|
| Cleared CSF with DTC 101 | 7 |
| Responders | |
| Breast cancer | 1 |
| Non-small cell lung cancer | 1 |
| Murdple Myeloma | 1 |
| CML in blast crisis | 1 |
| Melanoma | 1 |
| AIDS-related non-Hodgkin's lymphoma | 1 |
| Primitive neuroectodermal tumor | 1 |
| Non-Responders | |
| AIDS-related NHL | 1 |
| Primitive neuroectodermal tumor | 1 |

Three of twelve patients had evidence of neoplastic meningitis by CT or MRI scan, but had negative CSF cytology prior to therapy and were not evaluable for cytologic response. However, none of these three patients developed a positive CSF cytology while on treatment.

Surprisingly, responses were observed at all dose levels and were not limited to the higher doses. One patient with multiple myeloma relapsed following an initial cytologic response at the 25 mg dose level, then responded again to a higher dose (37.5 mg) of DTC 101. Three of five patients presenting with headache responded clinically to DTC 101 therapy. No clinical improvement was observed in patients with focal (ophthalmoplegia or paraparesis) or diffuse (acute confusional state) neurologic deficits at the start of therapy.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

We claim:

1. A method for ameliorating a viral disease which comprises intralumbar administration to the cerebrospinal fluid (CSF) of a human with the disease of a therapeutically effective amount of an antiviral drug in a synthetic membrane vesicle such that the antiviral agent persists in the cerebro-ventricular space for a time sufficient to ameliorate the disease.

2. The method of claim 1 wherein the synthetic membrane vesicle is a liposome.

3. The method of claim 2 wherein the synthetic membrane vesicle contains multiple concentric chambers.

4. The method of claim 3 wherein the synthetic membrane vesicle contains multiple non-concentric chambers.

5. The method of claim 1 wherein the antiviral agent is cytarabine.

* * * * *